United States Patent [19]
Broude et al.

[11] Patent Number: 5,717,198
[45] Date of Patent: Feb. 10, 1998

[54] PELLICLE REFLECTIVITY MONITORING SYSTEM HAVING MEANS FOR COMPENSATING FOR PORTIONS OF LIGHT REFLECTED BY THE PELLICLE

[75] Inventors: Sergey V. Broude, Newton Centre; Nicholas Allen, Bedford; Abdu Boudour, West Newton; Eric Chase, Carlisle; Carl Johnson, Tewksbury; Pascal Miller, North Chelmsford; Jay Ormsby, Salem, all of Mass.

[73] Assignee: QC Optics, Inc., Burlington, Mass.

[21] Appl. No.: 499,819

[22] Filed: Jul. 10, 1995

[51] Int. Cl.[6] .................................................. G01N 21/88
[52] U.S. Cl. ............... 250/205; 250/559.45; 250/559.46; 356/237
[58] Field of Search ............................ 250/205, 559.45, 250/559.46, 559.47, 559.48; 356/237, 431, 445

[56] References Cited

U.S. PATENT DOCUMENTS

| | | | |
|---|---|---|---|
| 4,999,510 | 3/1991 | Hayano et al. | 356/237 |
| 5,072,128 | 12/1991 | Hayano et al. | 356/237 |
| 5,416,594 | 5/1995 | Gross et al. | 356/237 |

*Primary Examiner*—Stephone Allen
*Attorney, Agent, or Firm*—Iandiorio & Teska

[57] ABSTRACT

A pellicle reflectivity monitoring system comprising a radiation source for directing radiation through a pellicle to an object to be inspected, a sensor device positioned to receive the portion of the radiation reflected by the pellicle, a processor, responsive to the sensor device, for determining the intensity of the portion of the radiation reflected by the pellicle, and a lens assembly, positioned in an optical path between the pellicle and the sensor device, for directing the portion of the radiation reflected by pellicles of different heights onto the sensor device. A comparator device compares the intensity of the radiation directed at the object to be inspected with the intensity of the portion of the radiation reflected by the pellicle and outputs a correction factor based on the comparison in order to compensate for the portion of the radiation reflected by the pellicle.

25 Claims, 3 Drawing Sheets

UV Chrome
Inspection Station

PELLICLE REFLECTIVITY MONITORING SYSTEM HAVING MEANS FOR COMPENSATING FOR PORTIONS OF LIGHT REFLECTED BY THE PELLICLE

FIELD OF THE INVENTION

This invention relates to an inspection system for a photolithographic mask, and more particularly to a system for monitoring and compensating for the reflectivity of a protective pellicle covering the mask.

BACKGROUND OF INVENTION

Photolithographic masks have a chrome pattern on a glass or quartz substrate and are used in the manufacture of thousands of semiconductor wafers during a production run in a "stepper" printing machine. It is critical that the surface of the mask be free of contaminating particles lest the images of the particles show up repeatedly on each wafer causing the same defect to appear on every wafer. Accordingly, the masks are typically inspected using very precise equipment shown, for example, in U.S. Pat. Nos. 4,943,734; 4,794,264; 4,794,265; and 5,389,794, incorporated herein by reference.

Photolithographic masks are inspected in some systems by delivering a laser beam to the mask, detecting the intensity of the beam scattered by defects on the mask and determining the presence, size and location of any defects on the mask. As a mechanical mask holder/spindle assembly moves the mask, the surface of the mask is illuminated by a laser beam directed to the surface and the scattering of the laser beam off the surface, detected by one or more sensors, is analyzed: the scattering off the surface is different if a defect or particle is present than if no particle or defect is present.

Most modern semiconductor lithography masks are protected from airborne contaminants by "pellicles", thin (0.8–3.0 μm) polymer membranes stretched over aluminum frames that are glued to the masks. The pellicle, however, reflects a portion of the laser beam directed at the mask, thus affecting the amount of light delivered to the mask, and consequently, the amount of light scattered by a defect to be detected by the sensors. Furthermore, scattered light is passing through and is partially reflected by the pellicle on its path to the detectors. The amount of light scattered by a defect depends on the size of the defect: small defects scatter less light than large defects. When the intensity of the laser beam which strikes a defect is not known and the scattered light is further attenuated by the pellicle, it is impossible to accurately determine the size of a defect by the amount of light scattered by it. Small defects may go undetected if the amount of light scattered by them is less than would be expected when they are struck by a laser beam of a certain known intensity.

SUMMARY OF INVENTION

It is therefore an object of this invention to provide a pellicle reflectivity monitoring system in which the measure of the intensity lost due to the pellicle reflectivity is detected and compensated for.

It is a further object of this invention to provide such a monitoring system which increases the laser beam power to make up for the energy lost due to the pellicle reflectivity.

It is a further object of this invention to provide such a monitoring system which amplifies the detector output to make up for the energy lost due to the pellicle reflectivity.

This invention results from the realization that while the pellicle on a photolithographic mask protects the mask from airborne contaminants, it also reflects a portion of the laser light used to detect defects on the surface of the mask resulting in inaccurate defect size determinations. If the amount of laser light reflected by the pellicle is monitored, the power of the laser beam incident on the mask can be increased or the output of the detectors can be amplified or the sensitivity of a flaw size determination circuit can be increased to accommodate for the loss of radiation due to the pellicle's reflectivity.

This invention features a pellicle reflectivity monitoring system comprising a radiation source for directing radiation through a pellicle to an object to be inspected, a sensor device positioned to receive the portion of the radiation reflected by the pellicle, means, responsive to the sensor device, for determining the intensity of the portion of the radiation reflected by the pellicle, and means, including a pair of spherical lenses, positioned in an optical path between the pellicle and the sensor device, for directing the portion of the radiation reflected by pellicles of different heights onto the sensor device. There are means, responsive to the means for determining, for compensating for the portion of the radiation reflected by the pellicle.

The means for compensating may include means for comparing the intensity of the radiation directed at the object to be inspected with the intensity of the portion of the radiation reflected by the pellicle, means for determining a correction factor based on the comparison, and means for increasing the power of the radiation by the correction factor.

The invention may include means, responsive to the sensor device, for supplying a compensation signal indicative of the intensity of the radiation reflected by the pellicle to means for detecting scattering of radiation off the object and to the radiation source and means, responsive to the means for determining, for adjusting at least one of the radiation source and an output of the means for detecting to compensate for the radiation reflected by the pellicle.

This invention also features a system which monitors power loss due to the reflection of radiation by a pellicle comprising a sensor device positioned to receive a portion of the radiation reflected by the pellicle, means for determining the intensity of the portion of the radiation reflected by the pellicle, means, including a pair of spherical lenses positioned in an optical path between the pellicle and the sensor device, for directing the portion of the radiation reflected by pellicles of different heights onto the sensor device, and means, responsive to the means for determining, for adjusting the intensity of the radiation to compensate for the radiation reflected by the pellicle.

This invention also features a method for compensating for the reflectivity of a pellicle, comprising the steps of directing radiation at an object to be inspected, the object being covered by the pellicle, sensing the radiation reflected by the pellicle, determining the intensity of the radiation reflected by the pellicle, directing radiation reflected at different heights to a sensor device used in the sensing step to accommodate pellicles of different heights, adjusting the radiation directed at the object to be inspected to compensate for the radiation reflected by the pellicle, and detecting the radiation scattered by the object to be inspected. The method also includes the steps of adjusting the sensitivity of a detector used in the detecting step to compensate for the radiation reflected by the pellicle, adjusting at least one of the radiation and the sensitivity of a detector used in the detecting step to compensate for the radiation reflected by the pellicle, and comparing the intensity of the radiation with the intensity of the radiation reflected by the pellicle, determining a correction factor based on the comparison and adjusting at least one of the radiation and the detecting means by the correction factor to compensate for the radiation reflected by the pellicle.

DISCLOSURE OF PREFERRED EMBODIMENT

Other objects, features and advantages will occur to those skilled in the art from the following description of a preferred embodiment and the accompanying drawings, in which.

Figure 1:
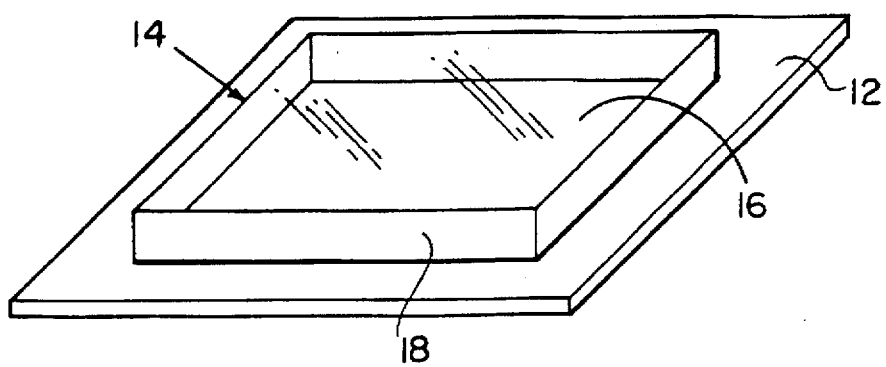
FIG. 1 is a three-dimensional diagram of a prior art photolithographic mask and a protective pellicle and frame which is glued to the top of the mask.

There is shown in FIG. 1 a photolithographic mask and pellicle assembly 10 which includes photolithographic mask 12 and pellicle 14. Pellicle 14 typically includes thin, nitrocellulose or other polymer film 16 tightly stretched over aluminum frame 18. Film 16 is typically 0.8–3 μm in thickness. Frame 18 is typically a black anodized aluminum material with edges between 1 mm and 3 mm wide. The frame 18 height typically ranges from 2–10mm. Photolithographic mask 12 is typically glass or quartz and ranges in size from 4"×4" to 8"×8" and is between 0.090" to 0.25" thick. Frame 18 of pellicle 14 is typically glued to mask 12 in order to form a permanent protective barrier for the mask surface against contaminants.

Figure 2:
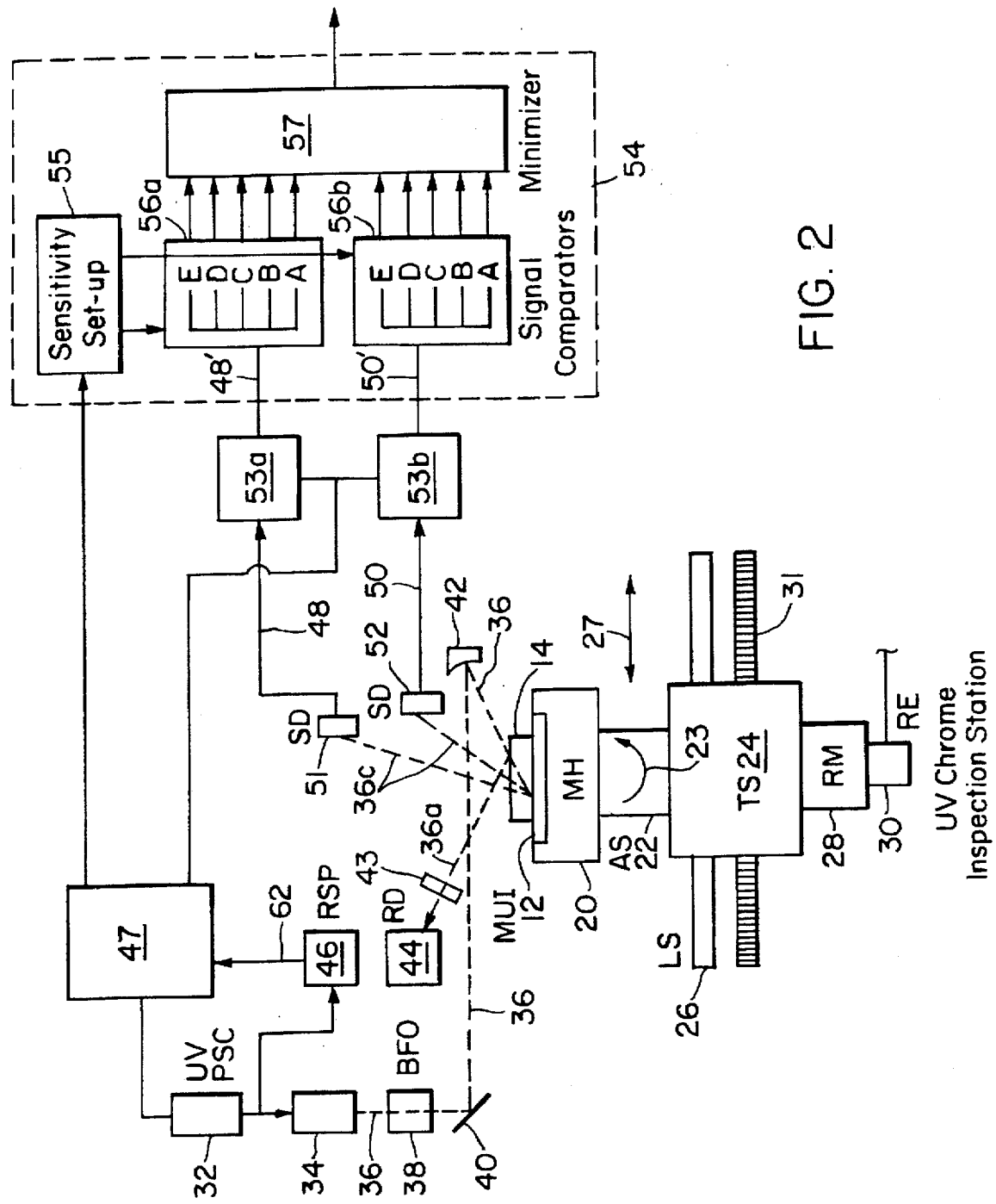
FIG. 2 is a schematic drawing of a photolithographic mask inspection station incorporating the pellicle reflectivity compensation system of this invention.

Photolithographic mask assembly 10 is inspected using the system shown in FIG. 2. Mask 12 is loaded into mask holder 20 fixed to air spindle 22 which rotates the mask during inspection in the direction shown by arrow 23. Translation stage 24 driven by motor 28 translates the inspection station along translation screw 26 in the direction shown by arrow 27 so that a spiral scan is effected. Rotation encoder 30 monitors the rotation of the spindle and translation encoder 31 monitors the translation of translation stage 24.

The pellicle reflectivity monitoring system of the present invention operates as follows. Power supply 32, FIG. 2, supplies power to source laser 34, such as the Coherent "Enterprise 653", which produces laser beam 36. Beam forming optics 38, including a prizmatic anamorphic expander and Galilean spherical expander, focus the beam on mirror 40 which directs beam 36 to focusing parabolic mirror 42. Focusing parabolic mirror 42 aims beam 36 at mask 12 through pellicle 14. While most of beam 36 passes through pellicle 14 to strike mask 12, a portion of the beam 36a is reflected from the pellicle 14 through lens assembly 43, described in more detail below, toward reflection sensor 44. Reflection sensor 44, such as a large area silicon photodiode, e.g., UDT220, senses beam 36a and provides a signal representing the intensity of reflected beam 36a to reflectometer signal processor 46 which processes the signal and controls laser power supply 32. Reflectometer signal processor 46 compares the power of the laser 34 with the power diverted from beam 36 by pellicle 14 as represented by beam 36a and outputs a correction factor to controller 47 which instructs power supply 32 to adjust the power of laser 34 by increasing it in order to compensate for the power lost through the reflection of light by pellicle 14. This correction factor takes into account both the loss of intensity of illumination beam 36 and the loss of scattered light 36c. Controller 47 is a microprocessor which can be programmed by the operator to direct the correction factor to at least one of power source 32, amplifiers 53a and 53b or sensitivity setup circuit 55. Lens assembly 43 directs reflected beam 36a at reflection sensor 44 regardless of variations in the height of pellicle 14. A more detailed description of the operation of lens assembly 43 and reflectometer signal processor 46 are set forth below.

Power supply 32 controls the output power of laser 34 in order to vary the intensity of laser beam 36 so that the power of the portion of the beam 36b which passes through pellicle 14 is adjusted according to the correction factor from controller 47. As shown in FIG. 2, laser beam 36 is divided into reflected beam 36a and non-reflected beam 36b. Beam 36b must be adjusted to an appropriate intensity so that when the beam strikes a defect on mask 12, the intensity of the light scattered as shown at 36c can be detected after passing again through the pellicle by scattering detectors 48 and 50 and the size of the defect determined from the intensity of the light scattered by the defect.

Alternatively, the correction factor output from reflectometer signal processor 46 can be provided by controller 47 to amplifiers 53a and 53b to amplify the outputs 48 and 50 of scattering detectors 51 and 52, thereby compensating for power lost due to pellicle 14. Amplified signals 48' and 50' are then provided to signal processor 54 which determines the size of flaws detected based on the amplitude of the outputs of scattering detectors 51 and 52. This allows reflectometer signal processor 46 to amplify the outputs 48 and 50 of the scattering detectors 51 and 52 by the correction factor instead of increasing the power of laser 36 by the correction factor.

The correction factor can also be provided by controller 47 to sensitivity setup circuit 55 which adjusts the sensitivity of comparators 56a and 56b. Comparators 56a and 56b receive outputs 48' and 50' from detectors 51 and 52 through amplifiers 53a and 53a and output a digital word indicative of the size of a detected flaw. Adjusting the sensitivity of comparators 56a and 56b allows signal processor 54 to output correct flaw size signals even though the amplitude of the scattering detected by detectors 51 and 52 has been decreased due to the reflection of the inspection beam 36 and the scattered light 36c by pellicle 14.

Amplifying the outputs of detectors 51 and 52 and increasing the sensitivity of comparators 56a and 56b is useful when, for example, the laser source is already operating at full power and it is not possible to increase the power of the laser. Amplifying the outputs of the scattering detectors or increasing the sensitivity of the comparators to follow the loss of light due to pellicle reflection allows the system to compensate for it. All of these approaches allow precise measuring of the size of defects on mask 12.

Figure 3:
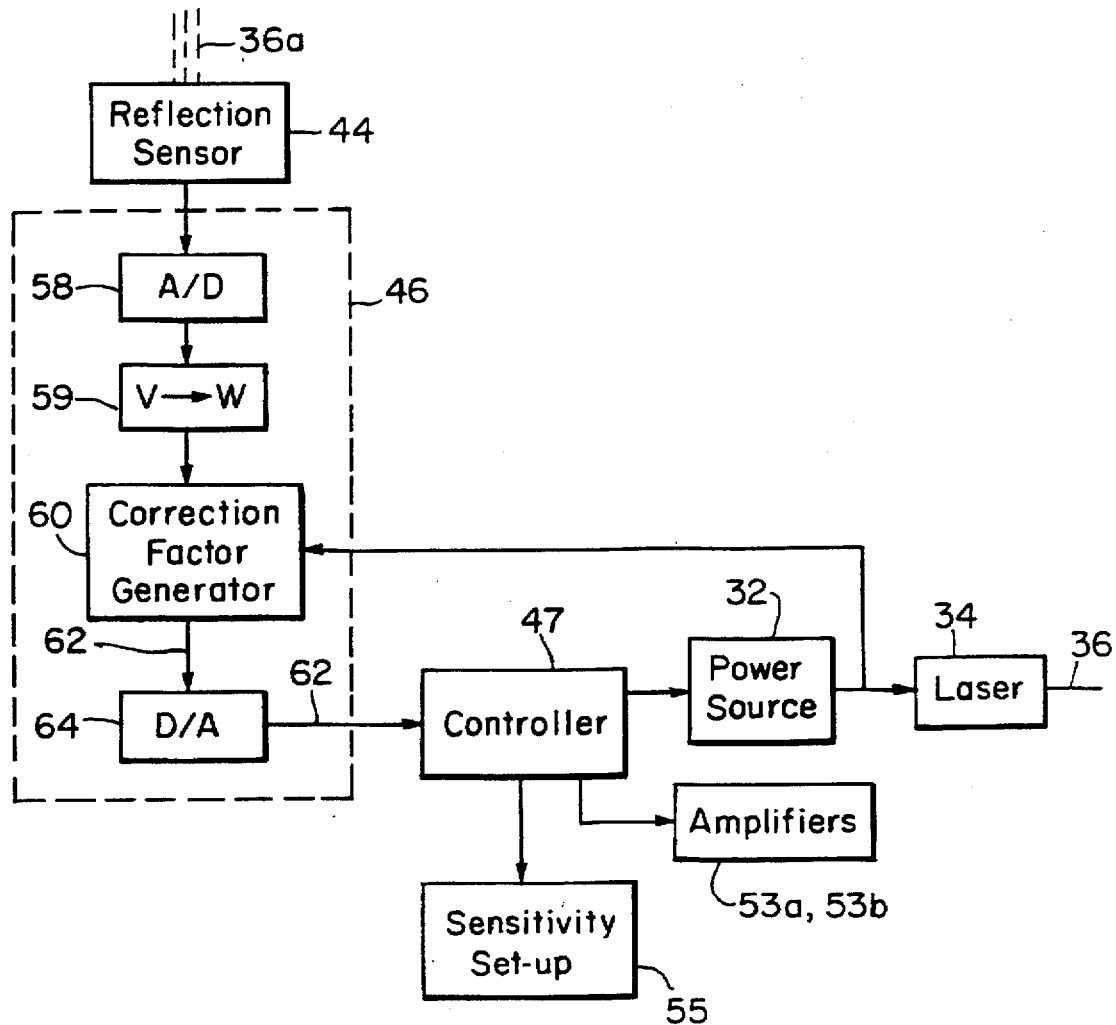
FIG. 3 is a schematic diagram of the reflectometer signal processor of the present invention.

Reflectometer signal processor 46, FIG. 2, is also shown in the block diagram in FIG. 3. Reflection sensor 44 outputs a voltage signal representing the amount of laser power reflected by pellicle 14 through beam 36a to analog to digital converter 58. The digital signal is then converted from voltage to power by voltage to power converter program 59.

Correction factor generator 60 compares the power of reflected beam 36a with the power input to source laser 34 and generates a correction factor on line 62 which is converted from digital to analog in D/A converter 64 and provided to either power supply 32, amplifier 53 or sensitivity circuit 55 through controller 47. Power source 32 can be instructed to increase the power of laser source 34 by the correction factor which represents the amount of power lost due to reflection, amplifier 53 can be instructed to amplify the outputs 48 and 50 of scattering detectors 51 and 52 by the correction factor and sensitivity setup circuit 55 can be instructed to increase the sensitivity of comparators 56a and 56b by the correction factor.

For example, if reflectometer detector 44 indicates that reflected beam 36a represents 10% of the total power of laser beam 36, meaning that only 90% of laser beam 36 is striking mask 12, correction factor generator 60 outputs the correction factor on line 62 through controller 47 which can be programmed to instruct power source 32 to increase the power to laser source 34 by approximately 20% in order to account also for the loss of the light scattered by the particle due to its reflection on the way to detectors 51 and 52. Other, more sophisticated and more precise algorithms, or empirical correction factors can be used. In the same way, the operator can program controller 47 to amplify the outputs 48 and 50 of scattering detectors 51 and 52 by approximately 20% to accommodate a 10% decrease in beam 36b incident on mask 12 or the operator can program controller 47 to instruct sensitivity setup circuit 55 to increase the sensitivity of comparators 56a and 56b by approximately 20%.

Figure 4:
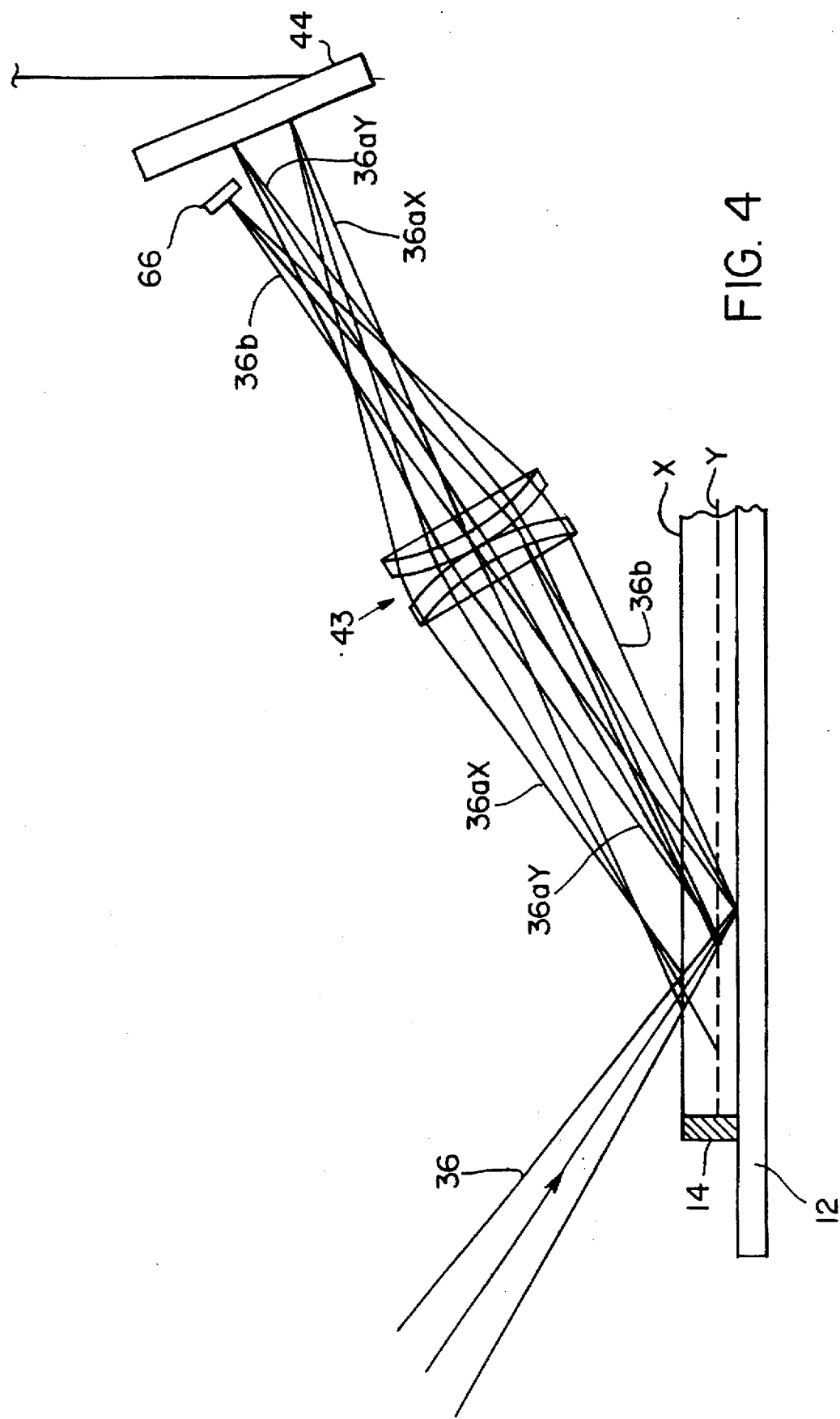
FIG. 4 is a schematic diagram showing the lens assembly which allows pellicles of different heights to be used in the present invention.

Typically, pellicle 14 can range in height from 2 to 10 min. Lens assembly 43, FIG. 4, accommodates pellicles of different heights by directing the reflected beam 36a at sensor 44 regardless of the height of the pellicle. When laser beam 36 strikes pellicle 14 of height X, beam 36aX is reflected toward detector 44. Reflected beam 36aX is directed by lens assembly 43 to ensure that it strikes sensor 44. When laser beam 36 strikes pellicle 14 of height Y, reflected beam 36aY is also directed by lens assembly 43 to ensure that it strikes sensor 44. Therefore, pellicles of different heights can be used without altering the height of reflection sensor 44.

In order to ensure that beam 36b reflected from the mask itself does not strike reflection sensor 44 and give a false power reading, lens assembly 43 directs beam 36b so that it strikes plate 66 which shields reflection sensor 44 from any beam which is reflected from mask 12 and not pellicle 14. Plate 66 simply absorbs beam 36b. Lens assembly 43 is formed by two spherical lenses with combined magnification factor close to 1.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A pellicle reflectivity compensation and monitoring system comprising:

a radiation source for directing radiation through a pellicle to an object to be inspected;

a sensor device positioned to receive the portion of the radiation reflected by said pellicle;

means, responsive to said sensor device, for determining the intensity of the portion of the radiation reflected by said pellicle;

means, positioned in an optical path between said pellicle and said sensor device, for directing the portion of the radiation reflected by pellicles of different heights onto said sensor device; and means, responsive to said means for determining, for compensating for the portion of the radiation reflected by said pellicle.

2. The system of claim 1 in which said means for compensating increases the output of a power source which drives said radiation source.

3. The system of claim 1 in which said means for compensating includes means for comparing the intensity of the radiation directed at the object to be inspected with the intensity of the portion of the radiation reflected by the pellicle, means for determining a correction factor based on said comparison, and means for increasing the power of said radiation by said correction factor.

4. The system of claim 1 in which said means for directing includes a pair of spherical lenses.

5. The system of claim 1 further including means, responsive to said means for determining, for adjusting said radiation source to compensate for the radiation reflected by the pellicle.

6. The system of claim 1 further including means, responsive to said means for determining, for supplying a compensation signal to said radiation source indicative of the intensity of the radiation reflected by said pellicle.

7. The system of claim 1 further including means for detecting scattering of the radiation off said object.

8. The system of claim 7 further including means, responsive to said means for determining, for amplifying an output of the means for detecting to compensate for the decrease in power of the radiation not reflected by the pellicle.

9. The system of claim 7 further including means, responsive to said means for detecting, for supplying a compensation signal to said means for detecting indicative of the intensity of the radiation reflected by the pellicle.

10. The system of claim 7 further including means, responsive to said means for determining, for adjusting at least one of said radiation source and an output of said means for detecting to compensate for the radiation reflected by said pellicle.

11. A system which monitors and compensates for power loss due to the reflection of radiation by a pellicle, the system comprising:

a sensor device positioned to receive a portion of the radiation reflected by the pellicle;

means for determining the intensity of the portion of the radiation reflected by the pellicle;

means, positioned in an optical path between said pellicle and said sensor device, for directing the portion of the radiation reflected by pellicles of different heights onto said sensor device; and means, responsive to said means for determining, for compensating for the portion of the radiation reflected by said pellicle.

12. The system of claim 11 in which said means for compensating increases the intensity of the radiation.

13. The system of claim 11 in which said means for compensating includes means for comparing the intensity of the radiation with the intensity of the portion of the radiation reflected by said pellicle, means for determining a correction factor, and means for increasing the intensity of said radiation by said correction factor.

14. The system of claim 11 in which said means for directing includes a pair of spherical lenses.

15. A pellicle reflectivity monitoring system comprising:

a radiation source for directing radiation through a pellicle to an object to be inspected;

a sensor device positioned to receive the portion of the radiation reflected by said pellicle;

means, responsive to said sensor device, for determining the intensity of the portion of the radiation reflected by said pellicle;

means for detecting scattering of the radiation off said object;

means, responsive to said means for determining, for adjusting at least one of said radiation source and an output of said means for detecting to compensate for the radiation reflected by the pellicle; and means, positioned in an optical path between said pellicle and said sensor device, for directing the portion of the radiation reflected by pellicles of different heights onto said sensor device.

16. The system of claim 15 in which said means for adjusting supplies a compensation signal to said means for detecting indicative of the intensity of the radiation reflected by the pellicle.

17. The system of claim 15 in which said means for adjusting supplies a compensation signal to said radiation source indicative of the intensity of the radiation reflected by said pellicle.

18. A pellicle reflectivity monitoring system comprising:

a radiation source for directing radiation through a pellicle to an object to be inspected;

a sensor device positioned to receive the portion of the radiation reflected by said pellicle;

means, responsive to said sensor device, for determining the intensity of the portion of the radiation reflected by said pellicle;

means, responsive to said means for determining, for adjusting said radiation source to compensate for the portion of the radiation reflected by said pellicle; and means, positioned in an optical path between said pellicle and said sensor device, for directing the portion of the radiation reflected by pellicles of different heights onto said sensor device.

19. A pellicle reflectivity monitoring system comprising:

a radiation source for directing radiation through a pellicle to an object to be inspected;

a sensor device positioned to receive the portion of the radiation reflected by said pellicle;

means, responsive to said sensor device, for determining the intensity of the portion of the radiation reflected by said pellicle;

means for detecting scattering of the radiation off said object;

means, responsive to said means for determining, for adjusting an output of said means for detecting to compensate for the radiation reflected by said pellicle; and means, positioned in an optical path between said pellicle and said sensor device, for directing the portion of the radiation reflected by pellicles of different heights onto said sensor device.

20. A method for monitoring and compensating for the reflectivity of a pellicle, the method comprising the steps of:

directing radiation at an object to be inspected, said object being covered by said pellicle;

sensing the radiation reflected by said pellicle;

determining the intensity of the radiation reflected by said pellicle;

directing radiation reflected at different heights to a sensor device used in said sensing step to accommodate pellicles of different heights; and adjusting the radiation directed at the object to be inspected to compensate for the radiation reflected by the pellicle.

21. The method of claim 20 further including the step of detecting the radiation scattered by the object to be inspected.

22. The method of claim 20 further including the step of adjusting an output of a detector used in said detecting step to compensate for the radiation reflected by said pellicle.

23. The method of claim 20 further including the step of adjusting at least one of the radiation and an output of a detector used in said detecting step to compensate for the radiation reflected by said pellicle.

24. The method of claim 20 further including the steps of comparing the intensity of said radiation with the intensity of the radiation reflected by said pellicle, determining a correction factor based on the comparison and adjusting at least one of said radiation and an output of a detector used in said detecting step by said correction factor to compensate for the radiation reflected by said pellicle.

25. The method of claim 20 further including the step of compensating for the portion of the radiation reflected by said pellicle.

* * * * *